United States Patent
Li et al.

(10) Patent No.: US 9,592,491 B2
(45) Date of Patent: Mar. 14, 2017

(54) ALUMINA CARRIER, METHOD OF PREPARING THE SAME, AND SILVER CATALYST

(71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(72) Inventors: Xianfeng Li, Beijing (CN); Jinbing Li, Beijing (CN); Xinxin Sun, Beijing (CN); Jianshe Chen, Beijing (CN); Shuyuan Cao, Beijing (CN); Lixin Gao, Beijing (CN); Hui Wang, Beijing (CN); Rujun Liang, Beijing (CN); Qian Xue, Beijing (CN); Zhixiang Zhang, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

( * ) Notice: Subject to any disclaimer, the term of this patent is extended or adjusted under 35 U.S.C. 154(b) by 0 days.

(21) Appl. No.: 14/525,635

(22) Filed: Oct. 28, 2014

(65) Prior Publication Data
US 2015/0119590 A1    Apr. 30, 2015

(30) Foreign Application Priority Data
Oct. 29, 2013   (CN) .......................... 2013 1 0523152

(51) Int. Cl.
| | |
|---|---|
| *B01J 21/04* | (2006.01) |
| *B01J 23/02* | (2006.01) |
| *B01J 23/10* | (2006.01) |
| *B01J 23/66* | (2006.01) |
| *C07D 301/10* | (2006.01) |
| *B01J 37/04* | (2006.01) |
| *B01J 37/26* | (2006.01) |
| *B01J 35/00* | (2006.01) |
| *B01J 35/10* | (2006.01) |
| *B01J 23/50* | (2006.01) |

(52) U.S. Cl.
CPC ............... *B01J 23/10* (2013.01); *B01J 21/04* (2013.01); *B01J 23/50* (2013.01); *B01J 23/66* (2013.01); *B01J 35/0026* (2013.01); *B01J 35/10* (2013.01); *B01J 35/1009* (2013.01); *B01J 35/1038* (2013.01); *B01J 35/1042* (2013.01); *B01J 37/04* (2013.01); *B01J 37/26* (2013.01); *C07D 301/10* (2013.01)

(58) Field of Classification Search
CPC ... B01J 21/04; B01J 23/10; B01J 23/50; B01J 23/66; B01J 35/0026; B01J 35/10; B01J 35/1009; B01J 35/1038; B01J 35/1042; B01J 37/04; B01J 37/26; C07D 301/10
USPC .................................. 549/534; 502/243, 439
See application file for complete search history.

(56) References Cited

U.S. PATENT DOCUMENTS

| | | | | |
|---|---|---|---|---|
| 5,958,824 A | * | 9/1999 | Rizkalla ................... | B01J 23/66 502/216 |
| 2007/0037991 A1 | * | 2/2007 | Rizkalla ................... | B01J 21/04 549/533 |

FOREIGN PATENT DOCUMENTS

| | | | |
|---|---|---|---|
| CN | 102553589 | * | 7/2012 |
| WO | 99/11371 A1 | | 3/1999 |

OTHER PUBLICATIONS

Search Report (PCT/ISA201) and Written Opinion (BE237A and BE237B), issued on Sep. 10, 2015, by the Belgian Office for Intellectual Property in corresponding Belgian Application No. BE 201400793 (9 pages).

* cited by examiner

*Primary Examiner* — T. Victor Oh
(74) *Attorney, Agent, or Firm* — Buchanan Ingersoll & Rooney PC

(57) ABSTRACT

The present disclosure discloses an α-alumina carrier, comprising the elements of lanthanum and silicon both dispersed in the interior and on the surface of the carrier. The mass ratio of the element of lanthanum to the element of silicon is in the range from 0.1:1 to 20:1. The inventors of the present disclosure have made extensive researches into the field of the silver catalyst and alumina carrier thereof, and added the elements of lanthanum and silicon (i.e., bulk phase addition) in preparing the alumina carrier used in the silver catalyst. The carrier thus obtained contains the elements of silicon and lanthanum both in the interior and on the surface thereof, and has improved specific surface area and strength. The silver catalyst prepared with the carrier can react in a low reaction temperature (has a high reaction activity) and has a high selectivity in producing ethylene oxide through oxidation of ethylene.

22 Claims, No Drawings

ALUMINA CARRIER, METHOD OF PREPARING THE SAME, AND SILVER CATALYST

FIELD OF THE INVENTION

The present disclosure relates to a carrier used in a silver catalyst, a method of preparing the same, and use thereof. Specifically, the present disclosure relates to an alumina carrier of a silver catalyst used in producing ethylene oxide through oxidation of ethylene. The present disclosure further relates to a catalyst comprising the above alumina carrier and use thereof.

BACKGROUND OF THE INVENTION

Ethylene is oxidized to produce ethylene oxide substantially in the presence of a silver catalyst, with side reactions to generate carbon dioxide, water, etc., wherein activity, selectivity, and stability constitute main performance indexes of the silver catalyst. Activity refers to a reaction temperature required at a certain reaction load in producing ethylene oxide. A lower temperature indicates a higher catalytic activity. Selectivity is the molar ratio of the ethylene which has been converted to ethylene oxide to the total amount of ethylene used in the reaction. And stability represents the decline rate of activity and stability, with a lower decline rate indicating a better stability.

Using a silver catalyst of high activity, high selectivity, and good stability in producing ethylene oxide by oxidation of ethylene can significantly improve economic efficiency. Therefore, it is a major direction in the art to prepare a silver catalyst of higher activity, higher selectivity, and better stability.

An existing method of preparing a silver catalyst comprises two steps: preparing a porous carrier (such as alumina) and adding active components and promoters to the carrier. Some new techniques of preparing silver catalyst carriers have been reported in recent years.

SUMMARY OF THE INVENTION

One object of the present disclosure is to provide an α-alumina carrier and a method of preparing the same. A silver catalyst containing the carrier or a carrier obtained through the method shows favorable activity (i.e., requires a relatively low reaction temperature) and superior selectivity in producing ethylene oxide by oxidation of ethylene.

Another object of the present disclosure is to provide a silver catalyst prepared using the above carrier.

Still another object of the present disclosure is to provide the use of the silver catalyst in producing ethylene oxide by oxidation of ethylene.

According to one aspect of the present disclosure, it provides an α-alumina carrier, comprising the elements of lanthanum and silicon both dispersed in the interior and on the surface of the carrier.

In one specific embodiment of the above carrier, the mass ratio of the element of lanthanum to the element of silicon is in the range from 0.1:1 to 20:1. In one specific embodiment, the mass ratio of the element of lanthanum to the element of silicon is in the range from 2:1 to 10:1, such as 2:1 to 9:1 and 2:1 to 8:1. The carrier obtained has high side crushing strength, low water absorption, and a high specific surface area, and therefore is beneficial for use thereof and for dispersion of active components loaded thereon. In one embodiment, the elements of lanthanum and silicon can be homogeneously dispersed in the interior and on the surface of the carrier, or can be homogeneously dispersed in the carrier.

In another specific embodiment of the above carrier, the total content of the elements of silicon and lanthanum accounts for 0.01 wt % to 3.0 wt %, preferably 0.01 wt % to 1.5 wt % (such as 0.02 wt % to 1.5 wt %, 0.03 wt % to 1.0 wt %, and 0.04 wt % to 0.7 wt %), and more preferably 0.1 wt % to 0.6 wt % of the carrier In the above carrier, the α-alumina carrier has one or more of the following characteristics:
1) a specific surface area in the range from 0.7 $m^2/g$ to 2.0 $m^2/g$,
2) a pore volume in the range from 0.35 ml/g to 0.85 ml/g,
3) water absorption equal to or higher than 30%,
4) side crushing strength in the range from 60 N/particle to 200 N/particle, and
5) a content of α-$Al_2O_3$ equal to or higher than 70 wt % based on the total weight of the carrier.

According to one aspect of the present disclosure, it provides a method of preparing the above α-alumina carrier, comprising the steps of:
I) preparing a mixture comprising the components of: a) trihydrate alumina in a particle size ranging from 50 meshes to 500 meshes, b) pseudo bohemite in a particle size equal to or greater than 200 meshes, d) a fluoride mineralizer, and e) lanthanum and/or a lanthanum-containing compound and silicon and/or a silicon-containing compound, and adding an acid solution into the mixture and kneading the acid solution and the mixture;
II) molding, drying, and calcining the resulting material in step I) to obtain the α-alumina carrier.

In one specific embodiment of the above method, the total content of the lanthanum and/or lanthanum-containing compound and silicon and/or silicon-containing compound (i.e., component e)), calculated on the basis of the elements of silicon and lanthanum, is in the range from 0.01 wt % to 3.0 wt %, preferably 0.01 wt % to 1.5 wt % (such as 0.02 wt % to 1.5 wt %, 0.03 wt % to 1.0 wt %, and 0.04 wt % to 0.7 wt %), and more preferably 0.1 wt % to 0.6 wt % of the total weight of the mixture; and the mass ratio of the lanthanum and/or lanthanum-containing compound to the silicon and/or silicon-containing compound based on the elements of lanthanum and silicon is in the range from 0.1:1 to 20:1, preferably 2:1 to 10:1, such as 2:1 to 9:1 and 2:1 to 8:1.

According to another specific embodiment of the above method, the lanthanum-containing compound is at least one selected from a group consisting of lanthanum oxide, lanthanum carbonate, lanthanum nitrate, lanthanum chloride, and lanthanum sulfate, preferably lanthanum oxide, lanthanum chloride, or both, while the silicon-containing compound is at least one selected from a group consisting of sodium silicate, tetraethyl orthosilicate, nano-silica, and silica gel, preferably tetraethyl orthosilicate, nano-silica or both.

According to one specific embodiment of the above method, the mixture contains component c): a heavy alkaline earth metal compound, the content of which is not higher than 1.5 wt %, preferably in the range from 0.1 wt % to 1.5 wt % based on the total weight of the mixture.

According to another specific embodiment of the above method, based on the total weight of the mixture, the contents of the trihydrate alumina (component a)), the pseudo bohemite (component b)), the fluoride mineralizer (component d)), and the acid solution are in the range from 40 wt % to 90 wt % (such as 44 wt % to 90 wt %), 5 wt % to 50 wt %, 0.1 wt % to 3.0 wt %, and 2 wt % to 60 wt %, preferably in the range from 65 wt % to 85 wt % (such as 65 wt % to 80 wt %), 10 wt % to 30 wt % (such as 10 wt % to 20 wt %), 1.0 wt % to 3.0 wt %, and 15 wt % to 20 wt %, respectively.

In the above method, in order to prepare the α-alumina carrier of the present disclosure, trihydrate alumina, i.e., component a) is to be used. The trihydrate alumina should be in a particle state with particle size thereof in the range from 50 meshes to 500 meshes, such as from 200 meshes to 500 meshes. Based on the total weight of the mixture in step I), the amount of trihydrate alumina is generally in the range from 40 wt % to 90 wt %, such as 44 wt % to 90 wt %, 65 wt % to 85 wt %, 65 wt % to 80 wt %, and 73 wt % to 77 wt %.

In one embodiment of the above method, in order to prepare the α-alumina carrier of the present disclosure, pseudo bohemite, i.e., component b) is to be used. The pseudo bohemite should be in a particle state with particle size thereof equal to or greater than 200 meshes, such as equal to or greater than 250 meshes, and from 200 meshes to 400 meshes. Based on the total weight of the mixture in step I), the amount of the pseudo bohemite as component b) is generally in the range from 5 wt % to 50 wt %, such as 10 wt % to 30 wt %, 10 wt % to 20 wt %, and 14 wt % to 16 wt %.

In another embodiment of the above method, addition of the fluoride mineralizer as component d) is to accelerate crystal transformation of the alumina. The fluoride mineralizer can be one or more selected from a group consisting of hydrogen fluoride, aluminum fluoride, ammonium fluoride, magnesium fluoride, and cryolite. The heavy alkaline earth metal compound as component c) can be one or more selected from a group consisting of oxides, sulfates, acetates, carbonates, nitrates, and oxalates of strontium or barium, preferably at least one selected from a group consisting of barium oxide, barium sulfate, barium nitrate, and barium carbonate. Based on the total weight of the mixture in step I), the amount of the heavy alkaline earth metal compound added is generally in the range from 0 wt % to 1.5 wt %, such as 0.1 wt % to 1.5 wt %, 0.1 wt % to 1.0 wt %, and 0.1 wt % to 0.5 wt %.

According to one specific embodiment of the present disclosure, the method comprises the following steps:

1) preparing a mixture comprising the following components:

a) 40 wt % to 90 wt %, such as 44 wt % to 90 wt %, of trihydrate alumina in a particle size ranging from 50 meshes to 500 meshes based on the total weight of the mixture, b) 5 wt % to 50 wt % of pseudo bohemite in a particle size equal to or greater than 200 meshes based on the total weight of the mixture, c) 0 wt % to 1.5 wt % of a heavy alkaline earth metal compound based on the total weight of the mixture, d) 0.1 wt % to 3.0 wt % of a fluoride mineralizer based on the total weight of the mixture, and e) 0.01 wt % to 3.0 wt % of lanthanum and/or a lanthanum-containing compound and silicon and/or a silicon-containing compound calculated on the basis of the elements of silicon and lanthanum;

II) adding 15 wt % to 60 wt % of a binder and water based on the total weight of the mixture into the above mixture, and kneading and molding the resulting material homogeneously to obtain a molded body; and III) drying the molded body obtained in step II) and calcining the same to obtain the α-alumina carrier.

In the above method, preferably, based on the total weight of the mixture, the amounts of components a) to e) are in the ranges from 65 wt % to 85 wt % (such as 65 wt % to 80 wt %), 10 wt % to 30 wt % (such as 10 wt % to 20 wt %), 0.1 wt % to 1.5 wt % (preferably 0.1 wt % to 1.0 wt %), 1.0 wt % to 2.0 wt %, and 0.01 wt % to 1.5 wt % (based on the elements in component e)), respectively. The adding amount of the binder and water is in the range from 15 wt % to 20 wt % of the total weight of the mixture.

In the above method, the binder, water, and pseudo bohemite in the mixture form an aluminum sol which binds the components together and become extrudable and moldable paste. In one specific embodiment of the above method, the binder is an acid, such as nitric acid, formic acid, acetic acid, propionic acid, and hydrochloric acid, preferably nitric acid, and more preferably nitric acid and water in a ratio from 1:1.25 to 1:10 by weight. In one specific embodiment, the ratio of the nitric acid to water is in the range from 1:2 to 1:4 by weight. The mixture of acid and water is the above mentioned acid solution.

In one specific embodiment of the above method, the acid, water, and pseudo bohemite can be partially or completely replaced by the alumina sol. Where partial replacement is adopted, the mixture comprises the alumina sol. That is, the alumina sol is used to replace a part of the pseudo bohemite, water, and acid. In this case, the amount of the acid can be properly reduced. The sum content of the pseudo bohemite and the alumina sol based on alumina accounts for 5 wt % to 50 wt %, preferably 10 wt % to 30 wt % of the total weight of the mixture. The weight of the alumina sol is calculated in the total weight of the mixture based on the weight of alumina. The contents of other components are as disclosed above.

According to another aspect of the present disclosure, it provides a method of preparing the above α-alumina carrier, comprising the steps of:

III) preparing and then kneading a mixture comprising the components of trihydrate alumina in a particle size ranging from 50 meshes to 500 meshes, an alumina sol, a fluoride mineralizer, and lanthanum and/or a lanthanum-containing compound and silicon and/or a silicon-containing compound; and IV) molding, drying, and calcining the resulting material in step III) to obtain the alumina carrier.

In one specific embodiment of the above method, the weight of the alumina sol is calculated in the total weight of the mixture on a basis of the alumina. According to one specific embodiment of the above method, calculated on a basis of the elements of silicon and lanthanum, the total content of the lanthanum and/or lanthanum-containing compound and silicon and/or silicon-containing compound accounts for 0.01 wt % to 3.0 wt %, preferably 0.01 wt % to 1.5 wt %, and more preferably 0.1 wt % to 0.6 wt % of the total weight of the mixture. The mass ratio of the lanthanum and/or lanthanum-containing compound to the silicon and/or silicon-containing compound based on the elements of lanthanum and silicon is in the range from 0.1:1 to 20:1, preferably 2:1 to 10:1, such as 2:1 to 9:1 and 2:1 to 8:1. According to another specific embodiment of the above method, the mixture contains a heavy alkaline earth metal compound; based on the total weight of the mixture, the content of the heavy alkaline earth metal compound is not higher than 1.5 wt %, preferably in the range from 0.1 wt % to 1.5 wt %. The contents of other components are as disclosed above.

In the preparation method of the present disclosure, the molded body after being dried is calcined at a temperature in the range from 1,000° C. to 1,500° C., preferably 1,000° C. to 1,400° C. for a period no less than 1 h, generally in the range from 2 h to 24, and preferably 2 h to 8 h. Almost all, for example more than 90%, of the alumina is converted into α-Al$_2$O$_3$ through calcining to obtain the α-Al$_2$O$_3$ carrier.

The α-alumina carrier prepared by the method of the present disclosure has the following characteristics: a specific surface area in the range from 0.7 m$^2$/g to 2.0 m$^2$/g, a pore volume in the range from 0.35 ml/g to 0.85 ml/g, water absorption equal to or higher than 30%, and side crushing strength in the range from 60 N/particle to 200 N/particle. Preferably, the α-alumina carrier has a content of α-Al$_2$O$_3$ equal to or higher than 70 wt % based on the total weight of the α-alumina carrier. The mass ratio of the element of lanthanum to the element of silicon in the carrier is in the range from 0.1:1 to 20:1, preferably 2:1 to 0:1, such as 2:1 to 9:1 and 2:1 to 8:1.

In the present disclosure, the specific surface area of the carrier is measured by the BET method using nitrogen physical adsorption according to the international testing standards ISO-9277. For example, a nitrogen physical adsorption meter (Quantachrome, NOVA2000e) can be used for measurement of the specific surface area of the carrier.

The pore volume of the carrier is measured by mercury intrusion porosimetry, for example, by a mercury injection apparatus (Micromeritics, AutoPore9510).

The interior and surface of the carrier obtained can be measured by an X-ray photoelectron spectrometer (Thermo-Fisher, ESCALab250). The result shows that the elements of lanthanum and silicon are contained both in the interior and on the surface of the carrier. Moreover, the content of the elements of lanthanum and silicon in the interior of the carrier is substantially the same as that of the elements of lanthanum and silicon on the surface thereof. It is thus proved that the elements of lanthanum and silicon are dispersed, and are almost homogeneously dispersed in the interior and on the surface of the carrier. In addition, the content of the elements of lanthanum and silicon in the carrier is substantially the same as the content of the elements of lanthanum and silicon that are added.

The amount of the alkaline earth metal compound in the carrier can be calculated or measured (for example by using X-ray fluorescence analysis).

The side crushing strength of the carrier can, for example, be measured by a DLII intelligent particle strength tester produced by Dalian Chemical Industrial Research and Design Institute. 30 particles of the carrier can be randomly selected as a sample and the side crushing strength thereof can be measured. An average value can be calculated to obtain the side crushing strength of the carrier.

Water absorption (ml/g) refers to the volume of water absorbed by per unit mass of the carrier in a saturated manner, and can be measured by the following method. A certain amount of the carrier ($m_1$) is first weighed out and then boiled for 1 h in boiling water. The carrier is then taken out and set up in wet gauze containing a moderate amount of water for adsorption of redundant water on the surface of the carrier. The mass of carrier after having adsorbed water is finally measured ($m_2$). The water adsorption can be calculated by the following formula: water adsorption=($m_2$−$m_1$)/$m_1$/$\rho_{water}$, wherein $\rho_{water}$ refers to the density of water at the temperature and atmospheric pressure when the measurement is being performed.

The mass ratio of lanthanum to silicon (La/Si) is calculated or tested (for example by X-ray fluorescence analysis).

The α-alumina carrier prepared by the method of the present disclosure can be in a routine form in the art, such as a ring, sphere, column, porous column, and others.

The elements of lanthanum and silicon are added in preparing the α-alumina carrier according to the method of the present disclosure, and are dispersed in the interior and on the surface of the carrier, namely, dispersed in the bulk phase of the carrier. The carrier thus obtained has high side crushing strength, low water absorption, and a high specific surface area, and therefore is beneficial for use thereof and for dispersion of an active component loaded thereon. In one specific embodiment, the α-alumina carrier of the present disclosure serves as the carrier of a silver catalyst used in epoxidation of ethylene to produce ethylene oxide.

According to another aspect of the present disclosure, it provides a silver catalyst used in producing ethylene oxide by oxidation of ethylene, comprising:

the above α-alumina carrier or an α-alumina carrier prepared by the above method, 1 wt % to 40 wt %, preferably 5 wt % to 25 wt % of a silver compound based on silver, 0 ppm to 2,000 ppm, preferably 5 ppm to 2,000 ppm, and more preferably 5 ppm to 1,500 ppm of an alkali metal additive based on the alkali metal, 0 ppm to 10,000 ppm, preferably 0 ppm to 8,000 ppm of an alkaline earth metal additive based on the alkaline earth metal, and 0 ppm to 2,000 ppm, preferably 10 ppm to 2,000 ppm, and more preferably 100 ppm to 1,000 ppm of a rhenium additive based on rhenium.

In one specific embodiment, the above silver catalyst can be prepared by the method comprising the following steps:

1) impregnating the above α-alumina carrier or an α-alumina carrier prepared by the above method in a solution containing a sufficient amount of a silver compound, organic amine, optional alkali metal additive, optional alkaline earth metal additive, optional rhenium additive, and optional co-additive of the rhenium additive, 2) leaching the impregnation liquid, and 3) activating the carrier obtained in step 2) in an oxygen-containing gas to obtain the silver catalyst.

In the present disclosure, the silver compound is silver oxide, silver nitrate, and/or silver oxalate, and the amount of the silver compound should ensure that the content of the element of silver accounts for 1 wt % to 40 wt %, preferably 5 wt % to 25 wt % of the total weight of the silver catalyst.

In the present disclosure, the alkali metal additive can be one or more selected from a group consisting of the compounds of lithium, sodium, potassium, rubidium, and cesium, preferably cesium sulfate, cesium nitrate, lithium nitrate, and/or potassium hydroxide, and more preferably cesium sulfate. In addition, the adding amount of the alkali metal additive in the impregnation liquid should ensure a content of the alkali metal in the silver catalyst in the range from 0 ppm to 2,000 ppm, preferably 5 ppm to 2,000 ppm, and more preferably 5 ppm to 1,500 ppm, based on the total weight of the silver catalyst.

In the present disclosure, the alkaline earth metal additive is one or more selected from a group consisting of the compounds of magnesium, calcium, strontium, or barium, for example one or more selected from a group consisting of oxides, oxalates, sulfates, acetates, and nitrates of magnesium, calcium, strontium, or barium. In addition, the adding amount of the alkaline earth metal additive in the impregnation liquid should ensure a content of the alkaline earth metal in the silver catalyst in the range from 0 ppm to 10,000 ppm, preferably 0 ppm to 8,000 ppm, such as 1 ppm to 8,000 ppm, based on the total weight of the silver catalyst.

In the present disclosure, the rhenium additive is one or more selected from a group consisting of rhenium oxides, perrhenic acid, cesium perrhenate, and ammonium perrhenate, preferably ammonium perrhenate. In addition, the adding amount of the rhenium additive in the impregnation liquid should ensure a content of the rhenium additive in the silver catalyst in the range from 0 ppm to 2,000 ppm, preferably 10 ppm to 2,000 ppm, and more preferably 100 ppm to 1,000 ppm based on the total weight of the silver catalyst. When the impregnation liquid contains the rhenium additive, a co-additive of the rhenium additive can be added to further improve activity, selectivity, and stability of the silver catalyst obtained. The co-additive of the rhenium additive of the present disclosure can be a compound of any transition metal in the periodic table of the elements, or can be a mixture of the compounds of several transition metals, preferably oxyacids and salts of an Group VIB or VIIB element, such as tungstic acid, sodium tungstate, potassium tungstate, ammonium tungstate, cesium tungstate, molybdic acid, ammonium molybdate, ammonium metatungstate, etc. The amount of the co-additive of the rhenium additive should ensure a content of the co-additive of the rhenium additive in the silver catalyst in the range from 0 ppm to 1,000 ppm, preferably 0 ppm to 500 ppm, based on the total weight of the silver catalyst.

In the present disclosure, the organic amine can be pyridine, butyl amine, ethylenediamine, 1,3-propylene diamine, ethanol amine, or a mixture thereof, preferably a mixture of ethylenediamine and ethanol amine.

To perform the impregnation in step 1), advantageously, the alumina carrier is impregnated into the impregnation liquid at a pressure lower than the atmospheric pressure, preferably at an absolute pressure lower than 10 mmHg for a period of 10 min to 60 min, followed by leaching of the impregnation liquid. The carrier obtained in step 2) is then activated in an oxygen-containing gas, i.e., to perform step 3) to obtain the silver catalyst. The activation in step 3) is favorably performed in air or a nitrogen-oxygen mixture with a content of oxygen not greater than 21% by volume, at a temperature in the range from 180° C. to 700° C., preferably 200° C. to 500° C., for a period of time in the range from 1 min to 120 min, preferably 2 min to 60 min.

According to another aspect of the present disclosure, it further provides a method of producing ethylene oxide by oxidation of ethylene, wherein ethylene is oxidized into ethylene oxide in the presence of the above silver catalyst. The silver catalyst presents favorable activity and selectivity in producing ethylene oxide by oxidation of ethylene.

The above and other purposes, features, and advantages of the present disclosure will become more explicit after reading the description of the present disclosure.

The inventors of the present disclosure have made extensive researches into the field of the silver catalyst and alumina carrier thereof, and added the elements of lanthanum and silicon (i.e., bulk phase addition) in preparing the alumina carrier used in the silver catalyst. The carrier thus obtained contains the elements of silicon and lanthanum both in the interior and on the surface thereof, and has improved specific surface area and strength. The silver catalyst prepared with the carrier can react in a low reaction temperature (has a high reaction activity) and has a high selectivity in producing ethylene oxide through oxidation of ethylene.

DETAILED DESCRIPTION OF THE EMBODIMENTS

The present disclosure will be further explained in conjunction with specific examples, which are not to limit the scope of the present disclosure.

The α-alumina carrier of the present disclosure is modified by the elements of lanthanum and silicon. The carrier can be used for producing ethylene oxide by oxidation of ethylene. In some embodiments, the mass ratio of the element of lanthanum to the element of silicon in the carrier is in the range from 0.1:1 to 20:1. In some embodiments, the mass ratio of the element of lanthanum to the element of silicon in the carrier is in the range from 0.5:1 to 2.5:1. In some embodiments, the mass ratio of the element of lanthanum to the element of silicon in the carrier is in the range from 3.0:1 to 4.5:1. In some embodiments, the mass ratio of the element of lanthanum to the element of silicon in the carrier is in the range from 5.0:1 to 7.5:1. In some embodiments, the mass ratio of the element of lanthanum to the element of silicon in the carrier is in the range from 8.0:1 to 12.0:1. In some embodiments, the mass ratio of the element of lanthanum to the element of silicon in the carrier is in the range from 2.0:1 to 10.0:1. In some embodiments, the mass ratio of the element of lanthanum to the element of silicon in the carrier is in the range from 2.0:1 to 9.0:1. In some other embodiments, the mass ratio of the element of lanthanum to the element of silicon in the carrier is in the range from 2.0:1 to 8.0:1.

Measurement of Catalytic Performance

The initial activity and selectivity of the silver catalysts involved in the present disclosure were measured by a laboratory microreactor (hereinafter "microreactor") evaluation device, which is a stainless steel tube with an inner diameter of 4 mm and is arranged in a heating jacket. The loading volume of the catalyst is 1 ml filled with an inert filler at a lower portion thereof, so that the catalyst bed is located in a constant temperature zone of the heating jacket.

The activity and selectivity measurement conditions employed in the present disclosure were as follows.

| Composition of the reaction gas (mol %) | |
|---|---|
| Ethylene ($C_2H_4$) | 28.0 ± 1.0 |
| Oxygen ($O_2$) | 7.4 ± 0.2 |
| Carbon dioxide ($CO_2$) | <3.0 |
| Ballast gas ($N_2$) | Balance |
| Inhibitor (dichloroethane) | Optimization |
| Reaction pressure | 2.1 MPa |
| Space velocity | 6,000/h |
| EO concentration at the outlet of the reactor | 2.5 mol % |
| Space time yield | 295 Kg EO/m³ Cat./h |

When the above reaction conditions were stably obtained, the composition of the gasses at the inlet and outlet of the reactor were constantly measured. The measurement results after applying volume shrinkage correction were used for calculation of the selectivity (S) by the following formula:

$$S = \frac{\Delta EO}{\Delta EO + 0.5 \times \Delta CO_2} \times 100\%.$$

In the above formula, ΔEO represents the differential concentration of ethylene oxide in the inlet gas and the outlet gas, and $\Delta CO_2$ represents the differential concentration of carbon dioxide in the inlet gas and the outlet gas. The average of 10 groups of test data was taken as the test result of the day.

Preparation of the Carrier

Example 1 (For Comparison)

A mixture of 372 g of trihydrate alumina having a particle size in the range from 200 meshes to 500 meshes, 112 g of pseudo bohemite having a particle size in the range from 200 meshes to 400 meshes, 3 g of $MgF_2$, and 0.5 g of $Ba(NO_3)_2$ were added into a mixer and homogeneously blended, and then transferred to a kneader, followed by addition of 90 ml of dilute nitric acid solution (the weight ratio of nitric acid to water being 1:3) into the kneader. The resulting mixture was kneaded into an extrudable and moldable paste, and extrusion molded into five-hole cylinder bodies, of which the outer diameter, length, and inner diameter were 8.0 mm, 6.0 mm, and 1.0 mm, respectively. The cylinder bodies were dried for 10 h at a temperature in the range from 80° C. to 120° C. to reduce the free water content thereof to be lower than 10 wt %, so as to prepare the green bodies of molded α-alumina carriers. The green bodies were then put into an electric furnace, which was heated from room temperature to 1,400° C. within 30 h and kept constant at this temperature for 2 h to obtain the white α-alumina carriers named Z-1. The side crushing strength, water adsorption, and specific surface area of Z-1 were measured and the results thereof are shown in Table 1.

Example 2 (For Comparison)

A mixture of 372 g of trihydrate alumina having a particle size in the range from 200 meshes to 500 meshes, 112 g of pseudo bohemite having a particle size in the range from 200 meshes to 400 meshes, 3 g of $MgF_2$, 0.5 g of $Ba(NO_3)_2$, and 0.51 g of $SiO_2$ were added into a mixer and homogeneously blended, and then transferred to a kneader, followed by addition of 90 ml of dilute nitric acid solution (the weight ratio of nitric acid to water being 1:3) into the kneader. The resulting mixture was kneaded into an extrudable and moldable paste, and extrusion molded into five-hole cylinder bodies, of which the outer diameter, length, and inner diameter were 8.0 mm, 6.0 mm, and 1.0 mm, respectively. The cylinder bodies were dried for 10 h at a temperature in the range from 80° C. to 120° C. to reduce the free water content thereof to be lower than 10 wt %, so as to prepare the green bodies of molded α-alumina carriers. The green bodies were then put into an electric furnace, which was heated from room temperature to 1,400° C. within 30 h and kept constant at this temperature for 2 h to obtain the white α-alumina carriers named Z-2. The side crushing strength, water adsorption, and specific surface area of Z-2 were measured and the results thereof are shown in Table 1.

Example 3 (For Comparison)

A mixture of 372 g of trihydrate alumina having a particle size in the range from 200 meshes to 500 meshes, 112 g of pseudo bohemite having a particle size in the range from 200 meshes to 400 meshes, 3 g of $MgF_2$, 0.5 g of $Ba(NO_3)_2$, and 0.58 g of $La_2O_3$ were added into a mixer and homogeneously blended, and then transferred to a kneader, followed by addition of 90 ml of dilute nitric acid solution (the weight ratio of nitric acid to water being 1:3) into the kneader. The resulting mixture was kneaded into an extrudable and moldable paste, and extrusion molded into five-hole cylinder bodies, of which the outer diameter, length, and inner diameter were 8.0 mm, 6.0 mm, and 1.0 mm, respectively. The cylinder bodies were dried for 10 h at a temperature in the range from 80° C. to 120° C. to reduce the free water content thereof to be lower than 10 wt %, so as to prepare the green bodies of molded α-alumina carriers. The green bodies were then put into an electric furnace, which was heated from room temperature to 1,400° C. within 30 h and kept constant at this temperature for 2 h to obtain the white α-alumina carriers named Z-3. The side crushing strength, water adsorption, and specific surface area of Z-3 were measured and the results thereof are shown in Table 1.

Example 4

A mixture of 372 g of trihydrate alumina having a particle size in the range from 200 meshes to 500 meshes, 112 g of pseudo bohemite having a particle size in the range from 200 meshes to 400 meshes, 3 g of $MgF_2$, 0.5 g of $Ba(NO_3)_2$, 0.58 g of $La_2O_3$, and 0.51 g of $SiO_2$ were added into a mixer and homogeneously blended, and then transferred to a kneader, followed by addition of 90 ml of dilute nitric acid solution (the weight ratio of nitric acid to water being 1:3) into the kneader. The resulting mixture was kneaded into an extrudable and moldable paste, and extrusion molded into five-hole cylinder bodies, of which the outer diameter, length, and inner diameter were 8.0 mm, 6.0 mm, and 1.0 mm, respectively. The cylinder bodies were dried for 10 h at a temperature in the range from 80° C. to 120° C. to reduce the free water content thereof to be lower than 10 wt %, so as to prepare the green bodies of molded α-alumina carriers. The green bodies were then put into an electric furnace, which was heated from room temperature to 1,400° C. within 30 h and kept constant at this temperature for 2 h to obtain the white α-alumina carriers named Z-4. The side crushing strength, water adsorption, and specific surface area of Z-4 were measured and the results thereof are shown in Table 1.

Example 5

The steps were the same as those in Example 4 except that the mixture contained 1.14 g of $La_2O_3$, and the white α-$Al_2O_3$ carrier obtained was named Z-5. The side crushing strength, water adsorption, and specific surface area of Z-5 were measured and the results thereof are shown in Table 1.

Example 6

The steps were the same as those in Example 4 except that the mixture contained 1.71 g of $La_2O_3$, and the white α-$Al_2O_3$ carrier obtained was named Z-6. The side crushing strength, water adsorption, and specific surface area of Z-6 were measured and the results thereof are shown in Table 1.

Example 7

The steps were the same as those in Example 4 except that the mixture contained 2.28 g of $La_2O_3$, and the white α-$Al_2O_3$ carrier obtained was named Z-7. The side crushing strength, water adsorption, and specific surface area of Z-7 were measured and the results thereof are shown in Table 1.

TABLE 1

Physical property data of the carriers

| | Sample of the carrier | | | | | | |
|---|---|---|---|---|---|---|---|
| | Z-1 | Z-2 | Z-3 | Z-4 | Z-5 | Z-6 | Z-7 |
| Side crushing strength (N/particles) | 48 | 106 | 60 | 121 | 101 | 98 | 91 |
| Water adsorption (%) | 51.14 | 51.28 | 49.12 | 46.9 | 47.4 | 47.5 | 48.2 |
| Specific surface area ($m^2/g$) | 0.752 | 1.06 | 0.764 | 1.38 | 1.26 | 1.01 | 0.95 |
| La/Si (mass ratio) | 0 | 0 | — | 2.03 | 4.09 | 6.13 | 8.17 |

Table 1 indicates that the alumina carrier of the present disclosure has significantly improved side crushing strength and reduced water adsorption, which is beneficial for used of the carrier. The alumina carrier of the present disclosure has a significantly improved specific surface area which can facilitate dispersion of silver.

Preparation of the Catalyst

Example 8 (For Comparison)

700 g of silver nitrate was taken and dissolved in 750 ml of deionized water to obtain a solution. 325 g of ammonium oxalate was taken and dissolved into 250 ml of deionized water at 50° C. to obtain a solution. The above two solutions were mixed under violent stirring to generate a white precipitate of silver oxalate. After 1 h of aging treatment, filtration was performed and the filter cake obtained was washed with deionized water until there was no nitrate ion in the filtrate. A filter cake of a silver oxalate paste, which contained 60 wt % of the metal silver and 15 wt % of water, was thus obtained.

300 g of ethylenediamine, 110 g of ethanol amine, and 375 g of deionized water were added into a glass flask having a stirrer to obtain a mixed solution. The silver oxalate paste prepared above was slowly added into the mixed solution under stirring at a temperature kept in the range from −5° C. to 10° C., so as to enable complete dissolution of the silver oxalate. Subsequently, 2.2 g of cesium sulfate and 1.4 g of strontium acetate were added, which preceded addition of deionized water so that the total mass of the solution reached 2,000 g. Thus, impregnation liquid M, which contained 22 wt % of silver, was prepared for use.

100 g of the sample of Z-1 prepared in Example 1 was taken and put into a container that could be vacuum pumped. The absolute pressure in the container was pumped to be lower than 10 mmHg and impregnation liquid M prepared above was added to impregnate the carrier for a period of 30 min. Next, redundant solution was removed through leaching. The carrier after being impregnated was heated for 5 min in an air flow at 350° C., and then cooled down to obtain a silver catalyst named CZ-1.

Example 9 (For Comparison)

The steps were the same as those in Example 8 except that 100 g of carrier Z-1 was replaced by 100 g of carrier Z-2, and the silver catalyst obtained was named CZ-2.

Example 10 (For Comparison)

The steps were the same as those in Example 8 except that 100 g of carrier Z-1 was replaced by 100 g of carrier Z-3, and the silver catalyst obtained was named CZ-3.

Example 11

The steps were the same as those in Example 8 except that 100 g of carrier Z-1 was replaced by 100 g of carrier Z-4, and the silver catalyst obtained was named CZ-4.

Example 12

The steps were the same as those in Example 8 except that 100 g of carrier Z-1 was replaced by 100 g of carrier Z-5, and the silver catalyst obtained was named CZ-5.

Example 13

The steps were the same as those in Example 8 except that 100 g of carrier Z-1 was replaced by 100 g of carrier Z-6, and the silver catalyst obtained was named CZ-6.

Example 14

The steps were the same as those in Example 8 except that 100 g of carrier Z-1 was replaced by 100 g of carrier Z-7, and the silver catalyst obtained was named CZ-7.

Example 15 (For Comparison)

The steps were the same as those in Example 8 except the following points. 2.41 g of $Na_2SiO_3 \cdot 9H_2O$ and 3.15 g of $LaCl_3 \cdot 7H_2O$ were added into impregnation liquid M to obtain an impregnation liquid containing the elements of silicon and lanthanum. 100 g of the carrier sample Z-1 prepared in Example 1 was taken and added into a container that could be vacuum pumped. The absolute pressure in the container was pumped to be lower than 10 mmHg, followed by addition of the impregnation liquid prepared above containing the elements of silicon and lanthanum to impregnate the carrier for 30 min. the redundant solution was then removed by leaching. The carrier after being impregnated was heated for 5 min in an air flow at 350° C., and then cooled down to obtain a silver catalyst named CZ-8.

The catalysts CZ-1, CZ-2, CZ-3, CZ-4, CZ-5, CZ-6, CZ-7, and CZ-8 prepared in Examples 8 to 14 were each analyzed for contents of silver and additives based on the metals, respectively. The results thereof show that the contents of silver and additives (caesium and strontium) among the catalysts were more or less the same with one another, respectively, wherein the contents of silver, caesium, and strontium were about 16.1 wt %, 360 ppm, and 280 ppm, respectively.

In addition, the activity and selectivity of each of the catalysts were measured by the microcreator evaluation device under the process conditions as described above under "Measurement of catalytic performance". The data above temperature and selectivity on the 7th day of the reaction were listed in Table 2.

TABLE 2

| Catalyst | Reaction temperature (° C.) | EO (mol %) | Selectivity (%) |
|---|---|---|---|
| CZ-1 | 230 | 2.51 | 83.41 |
| CZ-2 | 226 | 2.50 | 83.00 |
| CZ-3 | 223.5 | 2.50 | 83.25 |
| CZ-4 | 223 | 2.50 | 83.29 |
| CZ-5 | 221 | 2.51 | 83.59 |
| CZ-6 | 225 | 2.51 | 83.42 |
| CZ-7 | 228 | 2.50 | 83.43 |
| CZ-8 | 228 | 2.50 | 83.21 |

Table 2 indicates that, compared to an existing catalyst having a carrier which contains no silicon or lanthanum, the catalyst containing the carrier of the present disclosure has a lower reaction temperature, i.e., a significantly improved reaction activity, while keeping a high selectivity of the silver catalyst. Compared to a catalyst prepared by a carrier containing only silicon, the catalyst of the present disclosure possesses significantly improved selectivity while ensuring a low reaction temperature (i.e., a high reaction activity). Compared to a catalyst prepared by a carrier containing only lanthanum, the catalyst of the present disclosure possesses improved selectivity while ensuring a low reaction temperature (i.e., a high reaction activity). And compared to a catalyst impregnated with the elements of silicon and lanthanum on the surface thereof (CZ-8), the catalyst of the present disclosure has improved reaction activity and selectivity. Table 2 shows that compared to a catalyst containing only the element of silicon or lanthanum (CZ-2 or CZ-3), the catalyst of the present disclosure (CZ-4 to CZ-7) which contains the elements of silicon and lanthanum presents a synergistic effect, and can further improve selectivity while keeping a low reaction temperature (i.e., a high reaction activity).

It should be noted that the above examples are only used to explain, rather than to limit the present disclosure in any manner. Although the present disclosure has been discussed with reference to preferable examples, it should be understood that the terms and expressions adopted are for describing and explaining instead of limiting the present disclosure. The present disclosure can be modified within the scope of the claims, and can be amended without departing from the scope or spirits of the present disclosure. Although the present disclosure is described with specific methods, materials, and examples, the scope of the present disclosure herein disclosed should not be limited by the particularly disclosed examples as described above, but can be extended to other methods and uses having the same functions.

The invention claimed is:

1. A method of preparing an α-alumina carrier, comprising the steps of:
I) preparing a mixture comprising components of: a) trihydrate alumina in a particle size ranging from 50 meshes to 500 meshes, b) pseudo bohemite in a particle size equal to or greater than 200 meshes, d) a fluoride mineralizer, and e) lanthanum and/or a lanthanum-containing compound and silicon and/or a silicon-containing compound, and adding an acid solution into the mixture and kneading the acid solution and the mixture; and
II) molding, drying, and calcining the resulting material in step I) to obtain the α-alumina carrier;
wherein the α-alumina carrier comprises elements of lanthanum and silicon both dispersed in an interior and on a surface of the carrier.

2. The method of claim 1, wherein a mass ratio of the element of lanthanum to the element of silicon is in the range from 2:1 to 10:1.

3. The method of claim 1, wherein the total content of the elements of silicon and lanthanum accounts for 0.01 wt % to 3.0 wt % of the carrier.

4. The method of claim 1, wherein the α-alumina carrier has one or more of the following characteristics:
1) a specific surface area in the range from 0.7 m²/g to 2.0 m²/g,
2) a pore volume in the range from 0.35 ml/g to 0.85 ml/g,
3) water absorption equal to or higher than 30%,
4) side crushing strength in the range from 60 N/particle to 200 N/particle, and
5) a content of α-Al$_2$O$_3$ higher than 70 wt % based on the total weight of the carrier.

5. The method of claim 1, wherein the content of component e), calculated on the basis of the elements of silicon and lanthanum, is in the range from 0.01 wt % to 3.0 wt % of the total weight of the mixture.

6. The method of claim 1, wherein the mass ratio of the lanthanum and/or lanthanum-containing compound to the silicon and/or silicon-containing compound based on the elements of lanthanum and silicon is in the range from 2:1 to 10:1.

7. The method of claim 1, wherein the lanthanum-containing compound is at least one selected from the group consisting of lanthanum oxide, lanthanum carbonate, lanthanum nitrate, lanthanum chloride, and lanthanum sulfate, while the silicon-containing compound is at least one selected from the group consisting of sodium silicate, tetraethyl orthosilicate, nano-silicon, and silica gel.

8. The method of claim 1, wherein the mixture further contains component c): an alkaline earth metal compound, the content of which is not higher than 1.5 wt % based on the total weight of the mixture, and wherein the alkaline earth metal compound is at least one selected from the group consisting of oxides, sulfates, acetates, carbonates, nitrates, and oxalates of strontium or barium.

9. The method of claim 1, wherein based on the total weight of the mixture, the contents of the trihydrate alumina, the pseudo bohemite, the fluoride mineralizer, and the acid solution are in the range from 44 wt % to 90 wt %, 5 wt % to 50 wt %, 0.1 wt % to 3.0 wt %, and 2 wt % to 60 wt %, respectively.

10. The method of claim 1, wherein the mixture comprises an alumina sol, and the total content of the pseudo bohemite and the alumina sol based on alumina accounts for 5 wt % to 50 wt % of the mixture.

11. A method of preparing an α-alumina carrier, comprising the steps of:
I) preparing a mixture comprising components of: trihydrate alumina in the range from 50 meshes to 500 meshes, an alumina sol, a fluoride mineralizer, and lanthanum and/or a lanthanum-containing compound and silicon and/or a silicon-containing compound, and kneading the mixture; and
II) molding, drying, and calcining the resulting material in step I) to obtain the α-alumina carrier;
wherein the α-alumina carrier comprises elements of lanthanum and silicon both dispersed in an interior and on a surface of the carrier.

12. The method of claim 11, wherein calculated on a basis of the elements of silicon and lanthanum, the total content of the lanthanum and/or lanthanum-containing compound and silicon and/or silicon-containing compound based on the total weight of the mixture is in the range from 0.01 wt % to 3.0 wt %.

13. The method of claim 11, wherein the mass ratio of the lanthanum and/or lanthanum-containing compound to the silicon and/or silicon-containing compound based on the elements of lanthanum and silicon is in the range from 2:1 to 10:1.

14. A silver catalyst used in producing ethylene oxide through oxidation of ethylene, comprising:
an α-alumina carrier, the α-alumina carrier prepared by a method comprising the steps of:
I) preparing a mixture comprising components of: a) trihydrate alumina in a particle size ranging from 50 meshes to 500 meshes, b) pseudo bohemite in a particle size equal to or greater than 200 meshes, d) a fluoride mineralizer, and e) lanthanum and/or a lanthanum-containing compound and silicon and/or a silicon-containing compound, and adding an acid solution into the mixture and kneading the acid solution and the mixture; and
II) molding, drying, and calcining the resulting material in step I) to obtain the α-alumina carrier, or the α-alumina carrier prepared by a method comprising the steps of:
III) preparing a mixture comprising components of: trihydrate alumina in the range from 50 meshes to 500 meshes, an alumina sol, a fluoride mineralizer, and lanthanum and/or a lanthanum-containing compound and silicon and/or a silicon-containing compound, and kneading the mixture; and
IV) molding, drying, and calcining the resulting material in step III) to obtain the α-alumina carrier,
1 wt % to 40 wt % of a silver compound based on silver,
0 ppm to 2,000 ppm of an alkali metal additive based on the alkali metal,
0 ppm to 10,000 ppm of an alkaline earth metal additive based on the alkaline earth metal, and
0 ppm to 2,000 ppm of a rhenium additive based on rhenium;
wherein the α-alumina carrier comprises elements of lanthanum and silicon both dispersed in an interior and on a surface of the carrier.

15. A method of producing ethylene oxide by oxidation of ethylene, wherein ethylene is oxidized into ethylene oxide in the presence of the silver catalyst of claim 14.

16. The method of claim 1, wherein the elements of lanthanum and silicon are homogeneously dispersed in the interior and on the surface of the carrier.

17. The method of claim 1, wherein a mass ratio of the element of the lanthanum to the element of silicon is in the range from 2:1 to 20:1.

18. The method of claim 1, wherein a mass ratio of the lanthanum and/or lanthanum-containing compound to the silicon and/or silicon-containing compound based on the elements of lanthanum and silicon is in the range from 2:1 to 20:1.

19. The method of claim 11, wherein a mass ratio of the lanthanum and/or lanthanum-containing compound to the silicon and/or silicon-containing compound based on the elements of lanthanum and silicon is in the range from 2:1 to 20:1.

20. The method of claim 1, wherein a mass ratio of the element of lanthanum to the element of silicon is in the range from 2:1 to 10:1, and wherein the total content of the elements of silicon and lanthanum accounts for 0.01 wt % to 3.0 wt % of the carrier.

21. The method of claim 11, wherein a mass ratio of the element of lanthanum to the element of silicon is in the range from 2:1 to 10:1, and wherein the total content of the elements of silicon and lanthanum accounts for 0.01 wt % to 3.0 wt % of the carrier.

22. The silver catalyst of claim 14, wherein a mass ratio of the element of lanthanum to the element of silicon is in the range from 2:1 to 10:1, and wherein the total content of the elements of silicon and lanthanum accounts for 0.01 wt % to 3.0 wt % of the carrier.

* * * * *